US005348550A

United States Patent [19]

Ikeda et al.

[11] Patent Number: 5,348,550

[45] Date of Patent: Sep. 20, 1994

[54] DRUG VESSEL

[75] Inventors: Koji Ikeda, Osaka; Hitoshi Futagawa, Kusatsu; Toshihiro Kikuchi, Suita, all of Japan

[73] Assignee: Nissho Corporation, Osaka, Japan

[21] Appl. No.: 976,430

[22] Filed: Nov. 13, 1992

[30] Foreign Application Priority Data

Nov. 15, 1991 [JP] Japan .................................. 3-328100

[51] Int. Cl.5 ......................... B65D 39/00; A61M 5/32

[52] U.S. Cl. ..................................... 604/411; 215/364; 215/DIG. 3; 604/257

[58] Field of Search ........................ 215/14, 17, 18, 26, 215/28, 247, 248, 265, 266, 355, 364, DIG. 3, 249; 141/18, 21, 25, 26, 27, 28, 329, 330; 604/411, 415, 403, 251, 257; 220/751

[56] References Cited

U.S. PATENT DOCUMENTS

| | | | |
|---|---|---|---|
| 2,362,150 | 11/1944 | Odin | 215/266 |
| 2,652,054 | 9/1953 | Bishop | 220/751 X |
| 3,932,222 | 1/1976 | Dorn . | |
| 4,092,546 | 5/1978 | Larrabee . | |
| 4,234,083 | 11/1980 | Cohen . | |
| 4,325,368 | 4/1982 | Kaemmerer | 604/251 X |
| 4,583,971 | 4/1986 | Bocquet et al. . | |
| 4,614,267 | 9/1986 | Larkin . | |
| 4,757,911 | 7/1988 | Larkin et al. . | |
| 4,927,013 | 5/1990 | Brunt et al. . | |
| 4,936,841 | 6/1990 | Aoki et al. . | |
| 4,986,322 | 1/1991 | Chibret et al. | 141/319 |

FOREIGN PATENT DOCUMENTS

| | | |
|---|---|---|
| 0431779 | 6/1991 | European Pat. Off. . |
| 1171047 | 1/1959 | France . |
| 71680 | 1/1960 | France . |
| 1238156 | 6/1960 | France . |
| 1267855 | 12/1961 | France . |
| AH24375 | 1/1990 | Japan . |
| H2-26506 | 6/1990 | Japan . |

*Primary Examiner*—Allan N. Shoap
*Assistant Examiner*—Nova Stucker
*Attorney, Agent, or Firm*—Birch, Stewart, Kolasch & Birch

[57] ABSTRACT

A drug vessel includes a vessel body with a narrow neck extending to an open end of a mouth portion thereof, and a stopper fitted in the open end. The stopper includes a stopper body of an elastomeric material with a through-hole passing through a central portion thereof along its center axis, and a closing body fitted into the through-hole of stopper body to block the through-hole.

10 Claims, 4 Drawing Sheets

DRUG VESSEL

BACKGROUND OF THE INVENTION

FIELD OF THE INVENTION

The present invention relates to a drug vessel and, more particularly, a drug-containing vessel or vial which enables the drawing of a liquid medicine sterilely and easily therefrom without use of any hollow needles such as syringe needles.

DESCRIPTION OF THE PRIOR ART

In general, vessels or vials containing liquid medicines are sealed tightly by fitting a rubber stopper in a mouth of the vial. Thus, a liquid medicine contained in the vial is generally taken out therefrom, using a syringe fitted with a hollow needle for example. In this case, the hollow needle is pierced into the rubber stopper and then the syringe is operated to draw the liquid medicine from the vial through the hollow needle.

When piercing the needle into the rubber stopper, the rubber stopper is occasionally cored out or cut off by the pointed end of the hollow needle. Thus, there is a fear such that pieces of cored rubber stopper enter into the liquid medicine.

To solve such a problem, inventors of the present invention have proposed a drug vessel with an improved sealing means in U.S. patent Ser. No. 07/917,942, filed Jul. 24, 1992. This drug vessel includes a sealing means comprising an annular packing seated on a mouth portion of the vessel, a spherical closing body retained on the annular packing, and a cap-like holder having a through-hole to hold the spherical closing body in place.

However, the sealing means of such a drug vessel is complex in structure and difficult to assemble. In addition, it is required to cover the holder and the mouth portion of the vessel with a cap to insure sterile conditions of the drug vessel during transportation and storage.

SUMMARY OF THE INVENTION

It is therefore an object of the present invention to provide a drug vessel which is simple in structure and easy to assemble and which makes it possible to take out a liquid medicine contained therein with ease and sterility without use of any hollow needles such as syringe needles.

According to the present invention there is provided a drug vessel comprising a vessel body with a narrow neck extending to an open end thereof, and a stopper fitted in the open end of said vessel body, characterized in that said stopper comprises a stopper body of an elastomeric material with a through-hole passing through a central portion thereof along its center axis, and a closing body fitted into the through-hole of said stopper body to block the through-hole.

A drug to be contained in the drug vessel of the present invention may be liquid medicines, or solid or powdered medicines adapted to be dissolved in a solvent just before use to form a liquid medicine.

In one embodiment of the present invention, the stopper includes a retaining means for retaining the closing body forced out of the through-hole. Such a retaining means may be formed by provision of a retaining member on the bottom of the stopper body. In such a case, it is preferred to provide ribs on a bottom surface of the stopper to form a passage between the bottom surface of the stopper body and the closing body when the drug vessel is turned upside down after the closing body has been forced out of the through-hole.

The above and other objects, features and advantages of the present invention will become apparent from the following description taken in conjunction with the preferred embodiments thereof with reference to the accompanying drawings.

DETAILED DESCRIPTION OF THE PREFERRED EMBODIMENTS

Figure 1:
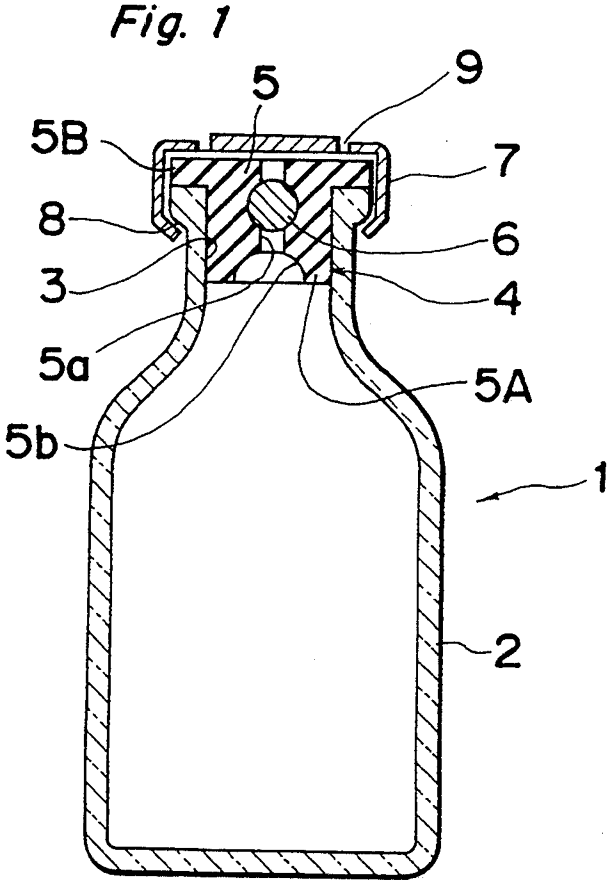
FIG. 1 is an axial sectional view of a drug vessel illustrating one embodiment of the present invention.

Referring now to FIG. 1, there is shown a drug vessel or vial of the present invention. The drug vessel, generally indicated by reference numeral 1, comprises a vessel body 2 with a narrow neck extending to an open end of a mouth portion 3 thereof, and a stopper 4 fitted in the mouth portion 3 of the vessel body 2 to close the same. The mouth portion 3 of the vessel body 2 is covered by a cap member 7 to retain the stopper 4 as well as to ensure sterile conditions of the drug vessel 1.

The vessel body 2 is made from glass or synthetic resin in the form of a bottom-closed cylinder with a narrow neck extending to its open end. When producing the vessel body 2 with synthetic resins, it is preferred to use transparent, chemical-resistant resins such as, for example, polypropylenes and polyesters. The vessel body 2 is provided at its mouth portion 3 with an annular projecting portion 8 for engagement with the cap member 7.

The stopper 4 comprises a stopper body 5 with a through hole 5*a*, and a closing body 6 fitted into the through-hole 5*a* of the stopper body 5.

The stopper body 5 is generally made of an elastomeric material such as, for example, butyl rubber, butadiene rubber, styrene-butadiene rubber, isoprene rubber and nitrile rubber so as to have a cylindrical plug portion 5A and a flange portion 5B integrally connected thereto. The plug portion 5A is so designed as to have a diameter slightly larger than the inside diameter of the mouth portion 3.

The stopper body 5 is provided with a through-hole 5*a* and a semispherical recess 5*b* in its central portion. The through-hole 5*a* passes through the central portion of the stopper body in its axial direction and is communicated with a top of the semispherical recess 5*b* formed in the lower part of the stopper body 5.

The closing body 6 is generally made with glass or a synthetic resin in the form of a spherical body having a diameter larger than that of the through-hole 5*a*. The spherical closing body 6 is fitted in the middle part of the through-hole 5*a* to block the same until just before use.

The cap member 7 is generally made of aluminum and fastened around the projecting portion 8 of the mouth portion of the vessel body 2 at a side wall thereof. A top wall of the cap member 7 is provided with a tearable portion 9 to provide access to the through-hole 5.

The above drug vessel 1 may be produced by placing a quantity of drug into the vessel body 2, forcing the stopper 4 into the mouth portion 3 of the vessel body 2 until the flange portion 5B of the stopper body 5 comes into close contact with the open end of the mouth portion 3, covering the mouth portion 3 of the vessel 2 with the cap member 7 to retain the stopper 4 as well as to prevent it from contamination with bacteria and dust.

If the drug is a solid or powdered medicine to be dissolved just before use, the stopper 4 is preferably provided with a retaining means for retaining the closing body 6 forced out of the through-hole 5, to prevent it from falling into the vessel body 2. Such a retaining means may be defined by a retaining chamber 10 provided on the bottom of the stopper body, as illustrated in FIGS. 2 and 3.

Figure 2:
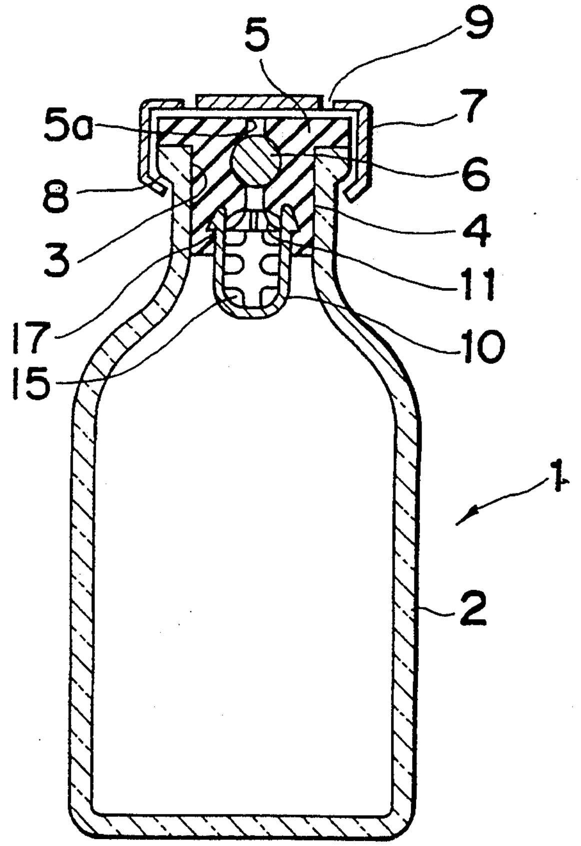
FIG. 2 is a cross sectional view similar to FIG. 1 illustrating another embodiment of the present invention.

Referring now to FIG. 2, there is shown a modified form of a drug vessel 1 according to the present invention. This drug vessel 1 has the same structure as that of the drug vessel of FIG. 1 except for that the stopper 4 further has a plurality of ribs 11 and includes a retaining member 10 of a chemical resistant resin. The retaining member 10 is fitted in an annular groove 17 formed in the plug portion 5A of the stopper body 5. Thus, in this embodiment, the retaining means is defined by the cylindrical retaining member 10. The retaining member 10 may be formed into a basket shape, or a cylindrical shape with a plurality of arc-shaped cuts 15 or bores so that it allows the liquid to pass therethrough but prevents the closing body 6 to pass therethrough.

The ribs 11 are formed as integral parts of the stopper body 2 and arranged radially at certain intervals along the semispherical surface of the recess 5*b* to form passages 16 for liquids between the spherical surface of the recess 5*b* and the closing body 6 rested thereon when the drug vessel is turned upside down after the closing body 6 is forced out of the through-hole 5. The provision of ribs 11 makes it possible to prevent the through-hole 5 from blockage by the closing body 6.

Figure 3:
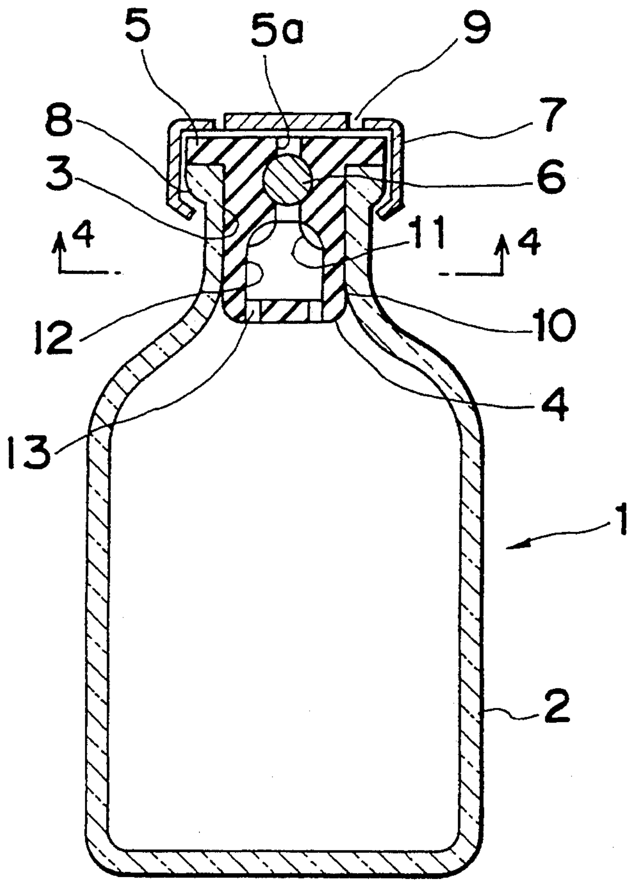
FIG. 3 is a cross sectional view similar to FIG. 1 illustrating still another embodiment of the present invention.
Figure 4:
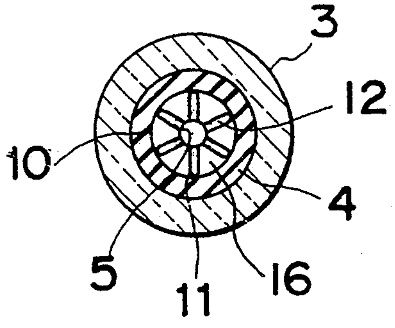
FIG. 4 is a cross sectional view of the drug vessel taken along the line 4—4 in FIG. 3.
Figure 5:
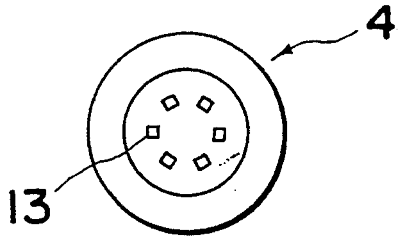
FIG. 5 is a bottom view of a stopper employed in the drug vessel of FIG. 3.

In another embodiment shown in FIG. 3 to FIG. 5, the stopper body 5 is provided with a retaining means 12 in its cylindrical plug portion 5A. The retaining means 12 is defined by the retaining chamber which is connected to the lower end of the through-hole 5 and communicated with the interior of the vessel body 2 through several holes 13 provided in the bottom of the retaining means 12.

The spherical top wall of the retaining means 12 is provided with a plurality of ribs 11 as integral parts of the stopper body 2, as best shown in FIG. 4. The ribs 11 are arranged radially at intervals to form passages 16. The passages 16 prevent the through-hole 5 from blockage caused by the closing body 6 when the drug vessel is turned upside down after the closing body 6 has been pushed out of the through-hole 5. The bottom wall of the retaining means 12 is provided with several holes 13 serving as passages for liquid, as shown in FIG. 5.

Figure 6:
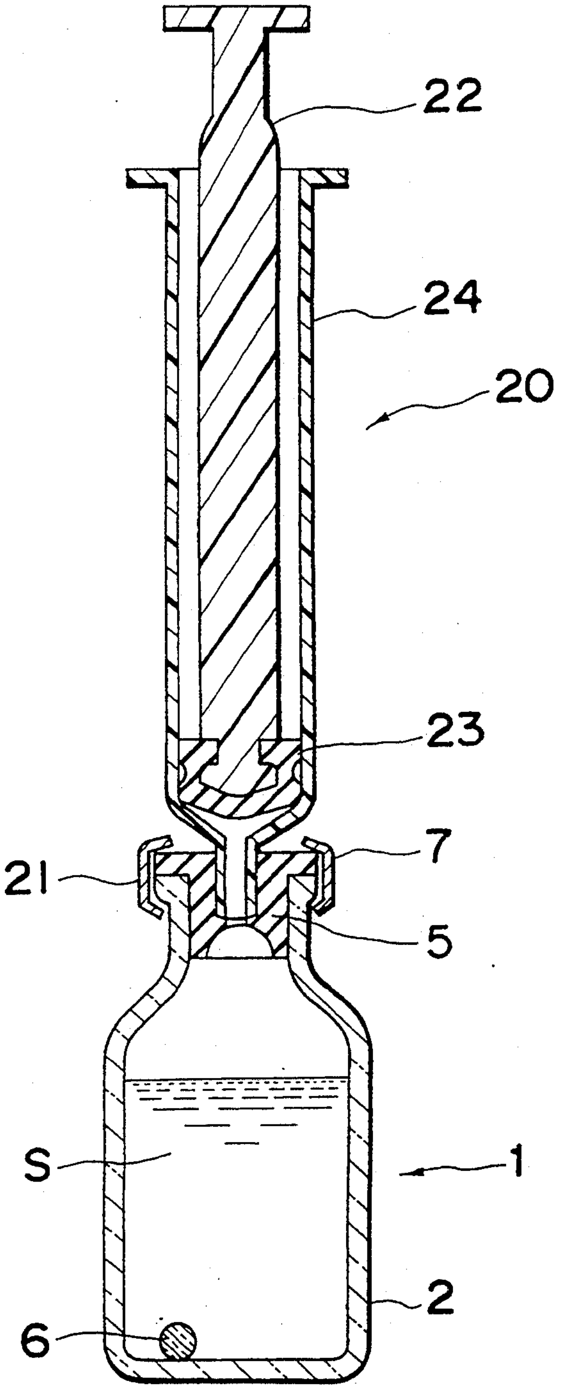
FIG. 6 is a side view, partially in section, showing a drug vessel of FIG. 3 with a syringe combined therewith.

In use, the drug vessel 1 is combined with a sterile syringe 20 consisting of a sterile cylinder 24 and a plunger 22 fitted with a gasket 23, as shown in FIG. 6. To make the drug vessel 1 ready for use, the mouth portion of the vessel is exposed to air by tearing off the central portion of the cap member 7 along the annular tear portion 9. Then, the tip 21 of the syringe 20 is forced into the through-hole 5 of the stopper 4 to push out the closing body 6 from the through-hole 5 into the vessel body 2, thereby communicating the interior of the syringe 20 with the vessel 1, as shown in FIG. 6. After turning the vessel 1 upside down together with the syringe 20, the plunger 22 of the syringe is pulled to draw in a quantity of liquid medicine S contained in the vessel 2.

As will be understood from the above, the drug vessel of-the present invention requires use of any hollow needles such as syringe needles to draw out the liquid medicine from the vessel, thus making it possible to prevent contamination of the drug with a strip of rubber stopper due to coring of the stopper.

Also, combined use of the drug vessel of the present invention and a syringe with no needle makes it possible to use a solid or powdered medicine adapted to be dissolved to prepare a liquid medicine just before use. In this case, a quantity of solvent or diluent is ejected forcibly from the syringe into the drug vessel of the present invention to prepare a drug solution, and then sucked into the syringe.

Figure 7:
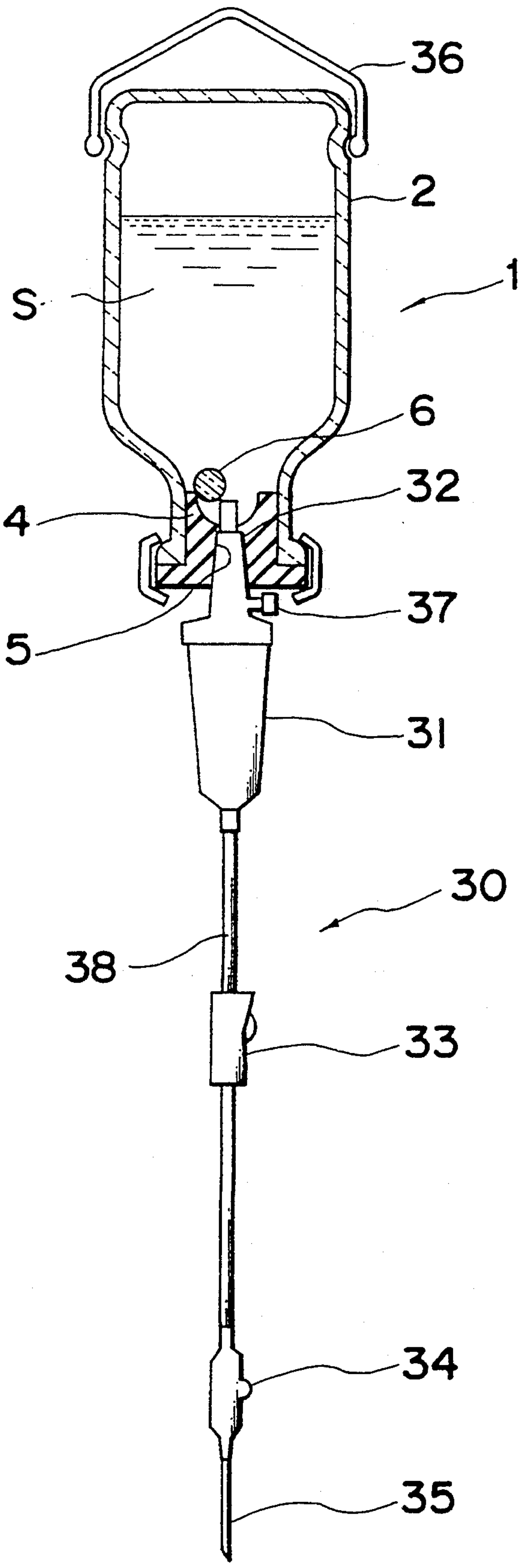
FIG. 7 is a side view, partially in section, showing a drug vessel of the present invention with an intravenous fluid administration set combined therewith.

The above drug vessel 1 may be used as a fluid container for dripping as shown in FIG. 7.

Referring now to FIG. 7, there is shown the drug vessel 1 combined with an intravenous fluid administration set 30 including a drip chamber 31 and a flexible tube 38 connected thereto. The drip chamber 31 is provided at its upper end with a tapered, tubular connecting member 32 including an air filter 37. The flexible tube 38 includes a clamp 33, an air trap 34 and a venous needle 35. The vessel body 2 is provided at its lower portion with a pair of recesses for attachment of a hanger 36.

In use, after tearing off the central portion of the cap member 7, the tubular connecting member 32 is forced into the through-hole 5*a* of the stopper 5 to push the closing body 6 into the vessel body 2, thereby communicating the drug vessel 1 with the interior of the intravenous fluid administration set 30. Then, the drug vessel is turned upside down as shown in FIG. 7 and the clamp 33 is released for intravenous drip infusion.

Although the present invention has been fully described in connection with the preferred embodiments thereof with reference to the accompanying drawings, it is to be noted that various changes and modifications are apparent to those skilled in the art. For example, the closing body may be used in the form of a cylindrical solid body or egg-shaped solid body. Further, the closing body may be made from any other materials, provided that it has a good chemical-resistance and provides a smooth surface. Such changes and modifications are to be understood as included within the scope of the present invention as defined by the appended claims unless they depart therefrom.

What is claimed is:

1. An intravenous drip infusion set comprising:

a drug vessel containing a drug and being composed of a vessel body having a mouth at one end thereof, a stopper of an elastomeric material fitted in said mouth, said stopper comprising a stopper body having a through-hole passing therethrough, and a spherical closing body press-fitted in said through-hole, said vessel body being provided in a lower portion of its outer wall with a pair of recesses and including a hanger attached to said pair of recesses, said stopper having a bottom surface with a semi-spherical recess coaxial with said through-hole; and a fluid administration set separated from said drug vessel but adapted to be combined therewith just before use, said fluid administration set comprising a drip chamber having, at one end thereof, a flexible tube connected thereto and, at the ether end, a tubular connecting member adapted to be forced into said through-hole of said stopper to push the closing body into the vessel body just before use.

2. The intravenous drip infusion set according to claim 1, wherein said stopper has a cylindrical plug portion and a flange integrated therewith, said plug portion having the through-hole and a diameter slightly greater than an inside diameter of said open end of the vessel body.

3. The intravenous drip infusion set according to claim 1, wherein said drip chamber is provided at its upper end with a tapered tubular member with an air filter.

4. The intravenous drip infusion set according to claim 3, wherein said flexible tube includes a clamp, an air trap and a venous needle.

5. The intravenous drip infusion set according to claim 1, wherein said drug vessel includes a retaining chamber for retaining the closing body when said closing body is forced out of the through-hole.

6. The intravenous drip infusion set according to claim 5, wherein a cap member is provided over said stopper with a tearable portion to provide access to the through-hole.

7. The intravenous drip infusion set according to claim 5, wherein said recess is provided with a plurality of ribs radially extending along a semispherical surface of the recess at certain intervals.

8. The intravenous drip infusion set according to claim 7, wherein said stopper body is provided with an annular groove at a bottom portion thereof and wherein said retaining means is defined by a retaining member fitted in said annular groove.

9. The intravenous drip infusion set according to claim 7, wherein said stopper body is provided with a retaining chamber connected to the lower end of the through-hole and communicated with the interior of the vessel body through several holes provided in the bottom of the retaining means.

10. A drug vessel having a stopper fitted in an open end thereof, said stopper comprising:

a stopper body of an elastomeric material with a longitudinal through-hole formed therein;

a closing body removably fitted in said through-hole for selectively blocking said through-hole; and a retaining chamber integrally formed with said stopper body for receiving said closing body upon dislodgement thereof from said through-hole, said retaining chamber including a plurality of fluid apertures formed therein such that receipt of said closing body will not block fluid flow to said through-hole.

* * * * *